United States Patent [19]
Katayama et al.

[11] Patent Number: 5,757,475
[45] Date of Patent: May 26, 1998

[54] ANALYZER FOR ANALYZING CASTS IN URINE WITH FLOW CYTOMETRY

[75] Inventors: Masayuki Katayama, Miki; Masakazu Fukuda; Hiroyuki Seshimo, both of Kobe, all of Japan

[73] Assignee: Toa Medical Electronics Co., Ltd., Hyogo, Japan

[21] Appl. No.: 767,783

[22] Filed: Dec. 17, 1996

[30] Foreign Application Priority Data

Dec. 19, 1995 [JP] Japan ................. 7-350714

[51] Int. Cl.$^6$ .................. G01N 21/00; G01J 3/30; G06F 15/00
[52] U.S. Cl. ............... 356/73; 356/318; 356/338; 364/413.11; 364/498
[58] Field of Search ............... 356/72,73, 318, 356/338; 364/413.01, 413.11

[56] References Cited

U.S. PATENT DOCUMENTS

| | | | |
|---|---|---|---|
| 3,844,662 | 10/1974 | Froreich | 356/246 |
| 4,622,298 | 11/1986 | Mansour et al. | 356/39 |
| 4,667,830 | 5/1987 | Nozaki, Jr. et al. | 356/72 |
| 4,992,365 | 2/1991 | Hyman | 435/34 |
| 5,325,168 | 6/1994 | Nakamoto et al. | 356/73 |

FOREIGN PATENT DOCUMENTS 0242971  10/1987  European Pat. Off.
4337459  11/1992  Japan.

*Primary Examiner*—Georgia Y. Epps
*Assistant Examiner*—Jason Vierra-Eisenberg
*Attorney, Agent, or Firm*—Greenblum & Bernstein P.L.C.

[57] ABSTRACT

An analyzer for analyzing urine material components is provided, which comprises: a sheath flow cell for forming a sample stream by surrounding a sample liquid containing preliminarily stained particles of the urine material components with a sheath fluid; a light source for illuminating the sample stream; a photodetector section for detecting optical information from the illuminated material component particles; and an analyzing section for analyzing the material components on the basis of the detected optical information; the analyzing section including a parameter extracting section for extracting a fluorescent light emission duration Flw and a scatter light emission duration Fscw as parameters from the detected optical information, a distribution diagram generating section for generating an Fscw-Flw scattergram, and a judging section for judging whether or not a material component particle being analyzed is a cast, on the basis of location of a data point of the material component particle in the generated scattergram.

6 Claims, 16 Drawing Sheets

ANALYZER FOR ANALYZING CASTS IN URINE WITH FLOW CYTOMETRY

BACKGROUND OF THE INVENTION

1. Field of the Invention

The present invention relates to an analyzer for analyzing urine material components and, more particularly, to an analyzer for analyzing blood cells, casts, epithelial cells, bacteria and the like in urine.

2. Description of Related Art

Hitherto known as particle analyzers are optical particle analyzers which are adapted to measure forward or lateral fluorescent light and scatter light from illuminated stained particles, and an electrical-resistance-type particle counter which is adapted to determine the numbers of particles on a size-by-size basis by inserting a needle member into an orifice (see Japanese Unexamined Patent Publication No. 4-337459 (1992) and European Unexamined Patent Publication No. 242971A2).

Where a urine sample is to be analyzed by means of such a prior art apparatus, however, the qualitative and quantitative analyses of particles of the urine material components are difficult because the urine sample contains many kinds of material component particles having complicated configurations and the number and form of the particles are liable to change. Particularly, it is difficult to discriminate cast particles from other material component particles on the basis of optical information typically employed in the prior art apparatus.

SUMMARY OF THE INVENTION

In view of the foregoing, it is an object of the present invention to provide an analyzer which is adapted to determine the number of cast particles and to judge whether or not a particle being analyzed is a cast and whether or not the cast contains inclusion, by employing improved optical information and a new parameter for the analysis.

In accordance with the present invention, there is provided an analyzer for analyzing urine material components which comprises: a sheath flow cell for forming a sample stream by surrounding a sample liquid containing preliminarily stained particles of the urine material components with a sheath fluid; a light source for illuminating the sample stream; a photodetecter section for detecting optical information from the illuminated material component particles; and an analyzing section for analyzing the material components on the basis of the detected optical information; the analyzing section including a parameter extracting section for extracting a fluorescent light emission duration Flw and a scatter light emission duration Fscw as parameters from the detected optical information, a distribution diagram generating section for generating an Fscw-Flw scattergram, a judging section for judging whether or not a material component particle being analyzed is a cast, on the basis of location of a data point of the material component particle in the generated scattergram.

DESCRIPTION OF THE PREFERRED EMBODIMENT

Figure 1:
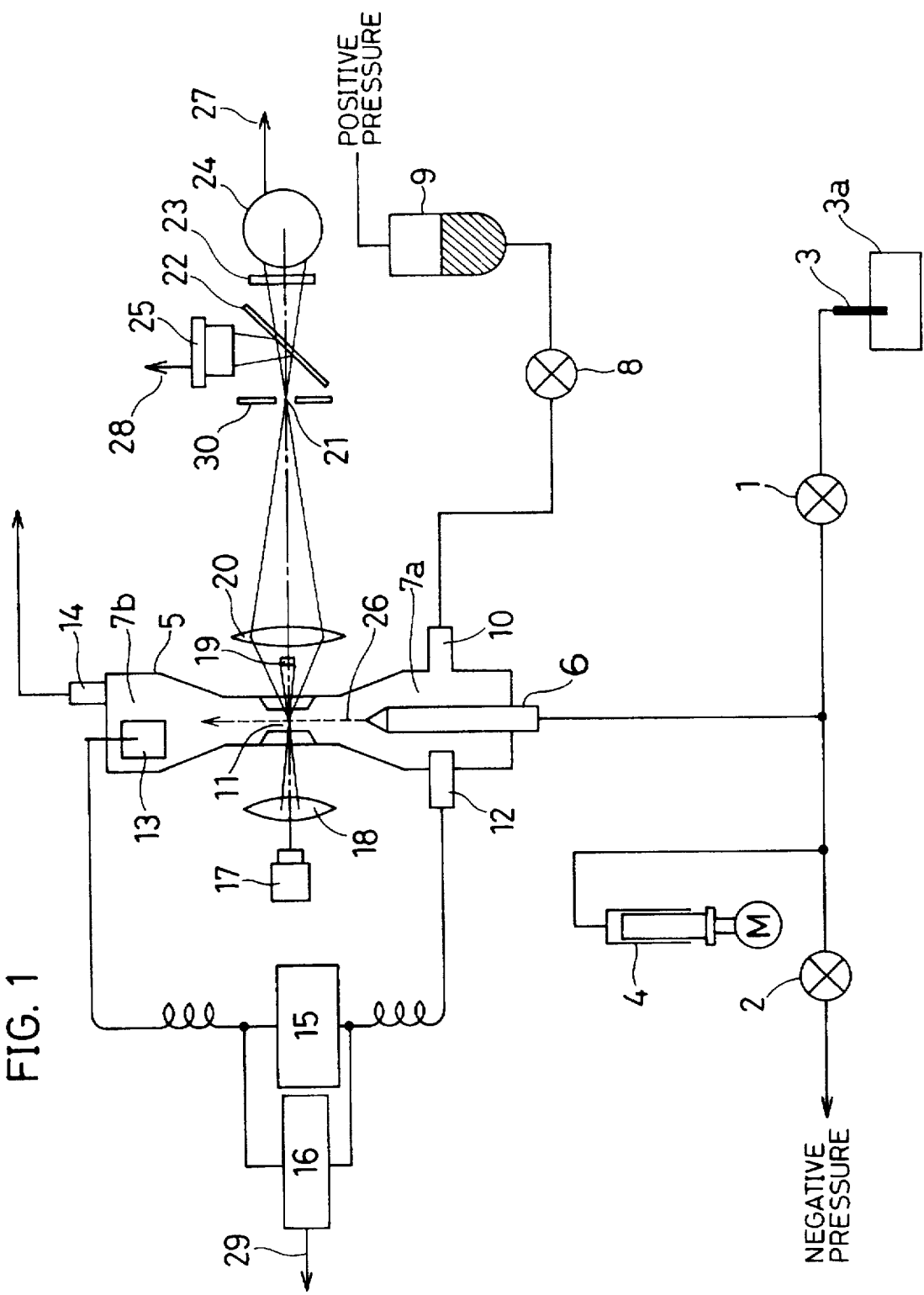
FIG. 1 is a schematic diagram illustrating the construction of an analyzer in accordance with one embodiment of the present invention.

Exemplary material components (particles) to be analyzed by means of the analyzer of the present invention include blood cells, crystals, casts, mucous threads, epithelial cells and bacteria contained in human urine. The particles of the urine material components are preferably pretreated with a fluorescent dye or other labeling agents. Accordingly, the analyzer may further include a pretreatment section for pretreating the particles of the urine material components with such a fluorescent dye or labeling agent before a urine sample is supplied to the sheath flow cell.

The blood cells include erythrocytes and leukocytes. The erythrocytes are often observed in urine sampled from patients of nephroureteric diseases, hemorrhagic diseases, leukemia and the like. The leukocytes are often observed in urine sampled from patients of nephric and ureteric infectious diseases, nephrophthisis and the like.

The crystals include crystals of uric acid, urates and calcium oxalate contained in acidic urine, and crystals of ammonium magnesium phosphate, calcium carbonate and ammonium urate contained in alkaline urine.

The casts are such that hemocytes and uriniferous epitheliocytes are enclosed in a base of Tomm-Horsfall mucoprotein agglutinated in uriniferous tubules in the presence of a small amount of plasma protein (albumin). The term "cast" comes from the fact that the casts are formed in the uriniferous tubules as a casting mold. The casts are also called "cylinders" in view of their shape. The presence of casts implies temporary occlusion of the uriniferous tubules, and is an important symptom suggesting a nephric disorder. Particularly, the detection of casts containing hemocytes, epitheliocytes and the like has an important clinical meaning.

The epithelial cells include squamous epitheliocytes and transitional epitheliocytes. The squamous epitheliocytes are extremely thin cells in a circular or polygonal shape exfoliated from the internal surface of urethra. The transitional epitheliocytes are cells having various shapes such as pare-like shape and spindle-like shape and constituting internal surfaces of renal pelvis, urethra, bladder and internal urethral opening.

The bacteria are herein meant by various bacteria contained in urine sampled from patients of urocystitis or pyelitis, for example.

The sheath flow cell according to the present invention preferably includes two cells, i.e., an upper cell and a lower cell, communicating through an orifice. The sheath flow cell is adapted to form a sample liquid containing particles into a sample stream by a hydrodynamic effect produced by surrounding the sample liquid with a sheath flow, whereby the particles in the sample liquid are passed in line through the orifice.

The sheath flow cell allows the sample liquid to pass through the orifice, for example, at a rate of 0.5 to 10 m/sec.

The light source projects a light beam from the outside of the flow cell to a particle passing through the orifice, a particle just entering the orifice, or a particle exiting out of the orifice. A laser light source (excluding a pulse light source) adapted for continuous illumination is preferably used as the light source in combination with a condenser lens. The width of the beam (measured in a flow direction) is preferably 5 to 30 µm.

The photodetecter section detects optical information, i.e., scatter light and fluorescent light from particles illuminated with the light beam, and converts the optical information into electrical pulse signals. Usable for the photodetecter section are a photodiode, a phototransistor, a photomultiplier tube and the like.

The analyzing section is preferably comprised of a microcomputer or a personal computer including a CPU, a ROM and a RAM.

The parameter extracting section extracts, for example, a fluorescent light intensity Fl and a scatter light intensity Fsc from peak amplitudes of the respective pulse signals indicative of the detected fluorescent light and scatter light, and extracts a fluorescent light emission duration (fluorescent light pulse width) Flw and a scatter light emission duration (scatter light pulse width) Fscw from pulse widths of the respective signals. More specifically, a peak hold circuit is employed for the extraction of the peak amplitudes, and a counter circuit is employed for the extraction of the pulse widths.

The extracted parameter data are each converted into distribution data F(X) in a parameter space. The distribution data is represented as frequency data F(X1, X2, . . . , Xm) at a point defined by coordinates (X1, X2, . . . , Xm) in an m-dimensional parameter space which is defined by m (e.g., 2) parameters X1, X2, . . . , Xm selected from n parameters Xn as required. The distribution diagram generating section generates a distribution diagram (scattergram) with the parameters X1, X2, . . . , Xm plotted as the coordinates.

The judging section may further have a function for judging whether or not the material component particle regarded as a cast is an inclusion cast, on the basis of the location of a data point of the material component particle in the scattergram.

If fluorescent light emission from one material component particle is intermittent, it is preferred that the parameter extracting section sums up intermittent fluorescent light emission periods (fluorescent light pulses) for determination of the fluorescent light emission duration Flw. In the case of the cast, the fluorescent light is emitted from inclusion bodies in the cast. This is why the fluorescent light emission from a single cast is intermittent. Therefore, the summation of the intermittent fluorescent light emission periods is required for the detection of accurate information concerning the inclusion bodies of the cast. The integral of the intermittent fluorescent pulses may be used instead, but affords less accurate information.

In accordance with another aspect of the present invention, an analyzer for analyzing urine material components comprises: a sheath flow cell for forming a sample stream by surrounding a sample liquid containing preliminarily stained particles of the urine material components with a sheath fluid; a light source for illuminating the sample stream; a photodetecter section for detecting optical information from the illuminated material component particles; and an analyzing section for analyzing the material components on the basis of the detected optical information; the analyzing section including a parameter extracting section for extracting a fluorescent light emission duration Flw and a scatter light emission duration Fscw as parameters from the detected optical information, and a computing section for calculating an Flw/Fscw value and judging whether or not a material component particle being analyzed is a cast, on the basis of the Flw/Fscw value. The judgment is based on the following principle. In the case of cells other than casts, the fluorescent light emission duration Flw and the scatter light emission duration Fscw are roughly equal to each other, since they are stainable with a fluorescent dye and emit fluorescent light when illuminated. On the other hand, base portions of the casts do not emit fluorescent light, but inclusion bodies in the casts emit fluorescent light. Therefore, the scatter light emission duration Fscw is greater than the fluorescent light emission duration Flw (Flw<Fscw). In the case of mucous threads which include no inclusion body, no fluorescent light is emitted and, therefore, the fluorescent light emission duration Flw is zero (Flw=0). It is preferred that data of the mucous threads are excluded from a cluster of data considered to be attributed to the casts on the basis of the scatter light intensity Fsc and the fluorescent light intensity Fl.

In such a case, the computing section may further have a function for judging whether or not the material component particle regarded as a cast is an inclusion cast, on the basis of the Flw/Fscw value. The fluorescent light emission duration Flw increases as the amount of the inclusion bodies in the cast increases. This means that the proportion of the inclusion bodies in the cast increases with an increase in the Flw/Fscw value.

Also, the analyzing section of the present invention may further comprise a function of discriminating hemolytic-state erythrocytes from other urine material components and computing the total number of erythrocytes including the hemolytic-state erythrocytes, on the basis of the generated distribution diagram.

In addition, the analyzing section of the present invention may further comprise a function of warning that data points of the other material components are possibly present in a domain of the predetermined material component in the distribution diagram when data points of the material components in the distribution diagram do not satisfy the discrimination condition.

The details of the above two functions are described in our copending U.S. patent application Ser. Nos. 08/767.782 and 08/767.784. filed Dec. 17, 1996, and EP patent applications entitled "ANALYZER FOR ANALYZING URINE MATERIAL COMPONENTS" corresponding to Japanese patent applications No. HEI 7(1995)-350712 and No. HEI 7(1995)-350713 filed on the same date as the Japanese patent application corresponding to the instant application, and are relied upon and incorporated by reference in this application.

The present invention will hereinafter be described by way of a preferred embodiment thereof with reference to the attached drawings. It should be noted that the present invention is not limited by the embodiment.

Figure 2:
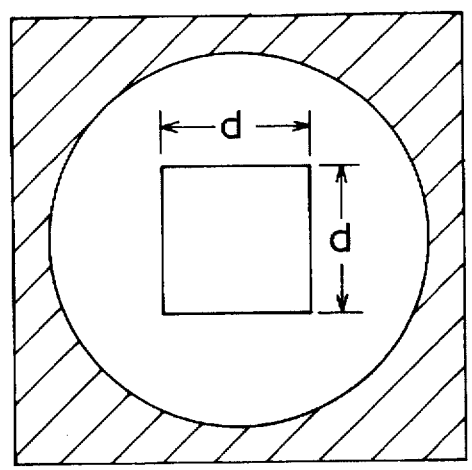
FIG. 2 is a sectional view of an orifice of a flow cell of the analyzer shown in FIG. 1.

FIG. 1 is a schematic diagram illustrating the construction of an analyzer according to one embodiment of the present invention. In FIG. 1, there is shown a flow cell 5 including a first cell 7a, a second cell 7b and an orifice 11 connecting the first and second cells 7a and 7b and having a cross section as shown in FIG. 2. The first cell 7a has a stainless negative electrode 12, a sample nozzle 6, and a supply port 10 from which a sheath fluid fed from a sheath fluid container 9 through a valve 8 is supplied into the first cell 7a. The second cell 7b has a platinum positive electrode 13, and a drain 14. In FIG. 1, there are also shown a suction nozzle 3 for sucking a sample liquid subjected to a pretreatment such as dilution or staining in a pretreatment section 3a, a syringe 4, and valves 1 and 2. A reference numeral 26 denotes a stream of the sample liquid injected from the sample nozzle 6.

A constant DC power supply 15 is connected between the electrodes 12 and 13. Provided in association with the power supply 15 is an amplifier 16 for amplifying an output voltage of the power supply 15 to output the amplified voltage as a signal 29.

An optical system includes an argon laser source 17, a condenser lens 18, a beam stopper 19, a collector lens 20, a light blocking plate 30 having a pin hole 21, a dichroic mirror 22, a filter 23, a photomultiplier tube 24 and a photodiode 25.

A diluent solution and a staining solution to be used for pretreatment are prepared in the pretreatment section 3a according to the prescription described below.

| Diluent solution | | |
|---|---|---|
| Buffer agent | HEPES | 50 mM |
| | NaOH | in an amount to adjust pH at 7.0 |
| Osmotic pressure compensating agent | sodium propionate | in an amount to adjust osmotic pressure at 150 mOsm/kg |
| Chelating agent | EDTA-3K | 0.4 W/W % |

The electric conductivity of the diluent solution is 5 mS/cm.
Staining solution

| First dye | DiOC6(3) | 400 ppm |
|---|---|---|
| Second fluorescent dye | EB | 1600 ppm |

Ethylene glycol is used as a solvent.

In the pretreatment section 3a, urine 400 µl is diluted in the above diluent solution 1160 µl, and the above staining solution 40 µl is added (dilution ratio=4) for staining the urine material components at 35° C.

When the valves 1 and 2 are opened for a predetermined period, the sample liquid (containing particles of the urine material components in accordance with this preferred embodiment) is sucked from the suction nozzle 3 by a negative pressure and filled in a conduit between the valves 1 and 2.

In turn, the syringe 4 pushes out the sample liquid from the conduit between the valves 1 and 2 at a constant rate, thereby injecting the sample liquid from the sample nozzle 6 into the first cell 7a. At the same time, the valve 8 is opened so that the sheath fluid is supplied into the first cell 7a.

Thus, the sample liquid is surrounded with the sheath fluid and narrowed down by the orifice 11 for formation of a sheath flow. The orifice 11 is formed of an optical glass (including quartz glass) and has a square opening (d=100 to 300 µm) as shown in FIG. 2.

The formation of the sheath flow allows particles in the sample liquid to be passed one by one in line through the orifice 11. The sample liquid and the sheath fluid passed through the orifice 11 are discharged from the drain 14.

The electrical resistance between the electrodes 12 and 13 is determined by the conductance (electrical conductivity) of the sheath fluid, the opening size (cross section) and length of the orifice 11, the conductance of the sample liquid, and the diameter of the sample liquid stream.

A constant current is passed between the electrodes 12 and 13 from the constant DC power supply 15 to generate a DC voltage, the amplitude of which is determined by the electrical resistance between the electrodes 12 and 13 and the amperage of the current. When the particles are passed through the orifice 11, the electrical resistance across the orifice 11 is changed. More specifically, only during the passage of the particles, the electrical resistance is changed, thereby pulsating the voltage generated between the electrodes 12 and 13. The maximum value of the pulsated voltage (peak amplitude of a pulse) is directly proportional to the size of a particle passing through the orifice 11. The pulse is amplified by the amplifier 16 and outputted as a resistance signal (analog pulse signal) 29.

On the other hand, a laser beam emitted from the laser source 17 is narrowed down as having an elliptical cross section by the condenser lens 18 and projected onto the sample liquid stream 26 flowing through the orifice 11. The minor axis of the elliptical cross section extending in the flow direction of the sample liquid stream is substantially equivalent to the diameter of a particle to be measured, e.g., about 10 µm, and the major axis extending perpendicular to the flow direction is sufficiently greater than the particle diameter, e.g., about 100 to 400 µm.

A portion of the laser beam passing through the flow cell 5 without impinging on the particle in the sample liquid is blocked by the beam stopper 19. Forward scatter light and forward fluorescent light from the particle illuminated with the laser beam are collected by the collector lens 20, and pass through the pin hole 21 of the light blocking plate 30, reaching the dichroic mirror 22.

The fluorescent light which has a greater wavelength than the scatter light passes through the dichroic mirror 22, and then passes through the filter 23, whereby scatter light is filtered away therefrom. The fluorescent light is detected by the photomultiplier tube 24, which outputs a fluorescent light signal (analog pulse signal) 27. The forward scatter light is reflected by the dichroic mirror 22, and then received by the photodiode 25, which outputs a scatter light signal (analog pulse signal) 28.

Figure 3:
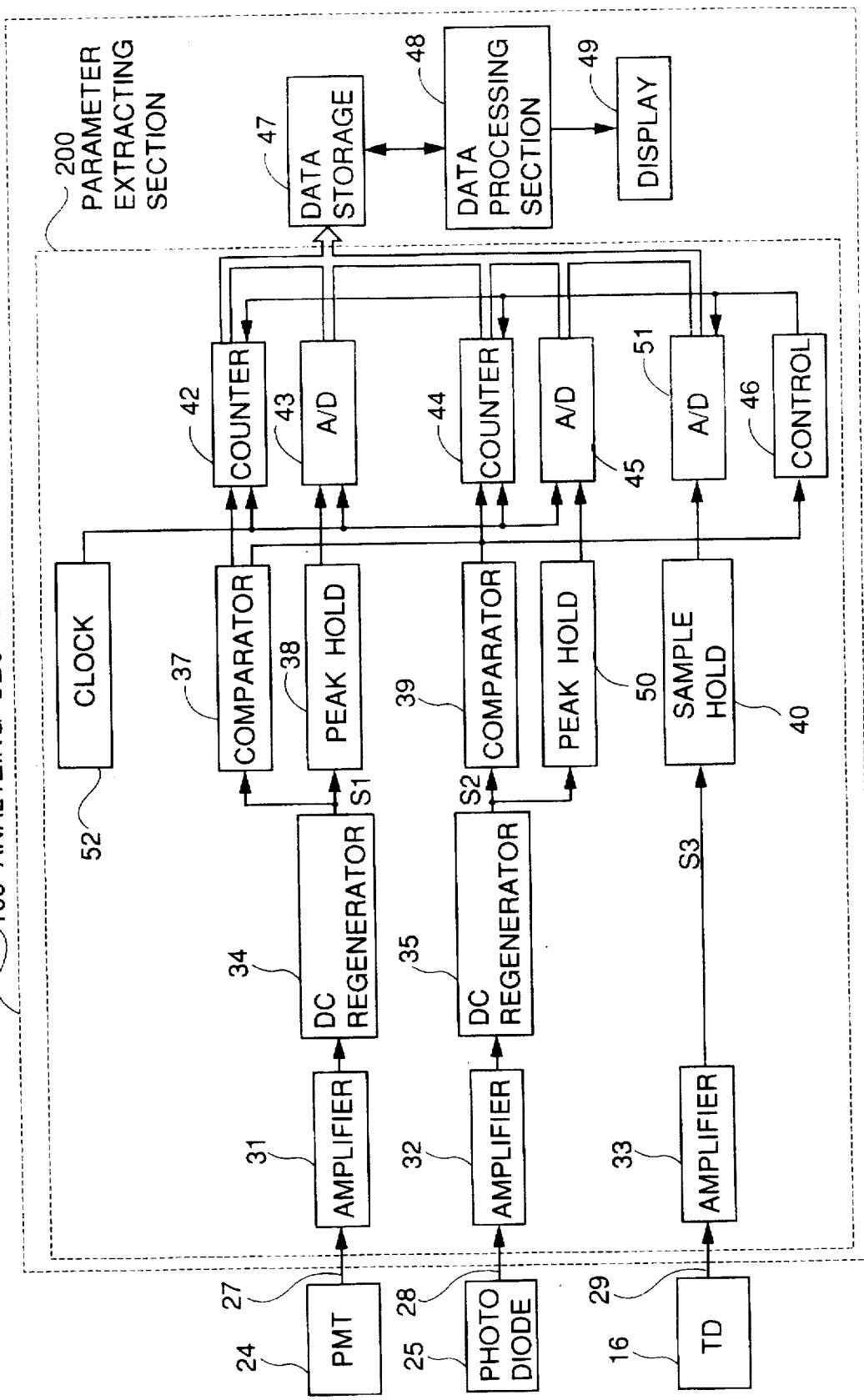
FIG. 3 is a block diagram illustrating the electrical construction of an analyzing section of the analyzer.

FIG. 3 is a block diagram illustrating the electrical construction of an analyzing section 100 which processes the fluorescent light signal 27, the scatter light signal 28 and the resistance signal 29 thus obtained. A parameter extracting section 200 includes amplifiers 31 to 33, direct current regenerator circuits 34 and 35, comparators 37 and 39, peak hold circuits 38 and 50, a clock generator 52, counters 42 and 44, A/D converters 43, 45 and 51, and a counter control circuit 46. In FIG. 3, there are also shown a data storage 47, a data processing section 48 and a display 49.

There will next be described a signal processing operation to be performed by the analyzing section having such a construction.

The scatter light pulse signal 28 is amplified by the amplifier 32, and the DC component thereof is fixed by the DC regenerator circuit 35. A pulse signal S2 outputted from the DC regenerator circuit 35 is compared with a threshold Th1 (see FIG. 22) by the comparator 39. A period (pulse width) during which the threshold Th1 is exceeded is measured as a scatter light emission duration (scatter light pulse width) Fscw by the counter 44. The peak amplitude of the scatter light signal is held by the peak hold circuit 50, and A/D-converted by the A/D converter 51 to provide a scatter light intensity Fsc.

The fluorescent light pulse signal 27 is amplified by the amplifier 31, and the DC component thereof is fixed by the DC regenerator circuit 34. A pulse signal S1 outputted from the DC regenerator circuit 34 is compared with a threshold Th2 (see FIG. 23) by the comparator 37. A period during which the threshold Th2 is exceeded is measured as a fluorescent light emission duration (scatter light pulse width) Flw by the counter 42. The peak amplitude of the fluorescent light signal 27 is held by the peak hold circuit 38, and A/D-converted by the A/D converter 43 to provide a fluorescent light intensity Fl.

The resistance pulse signal 29 is amplified by the amplifier 33. The peak amplitude thereof (pulse peak amplitude) is held by the sample hold circuit 40, and converted into a digital value by the A/D converter 45.

The digitized output signals of the counters 42 and 44 and the A/D converters 43, 45 and 51 are stored in the data storage 47 and, at the same time, sent to the data processing section 48 for determination of attribution of the respective urine material component particles.

More specifically, the attribution of the respective particles (erythrocyte, casts such as glass cast and inclusion cast, and the like) is determined on the basis of the distribution diagrams (histogram and scattergram). The particles in each category are counted, and the number thereof is converted on the basis of per-microliter sample liquid. The result and the distribution diagrams are displayed in the display 49.

Figure 4:
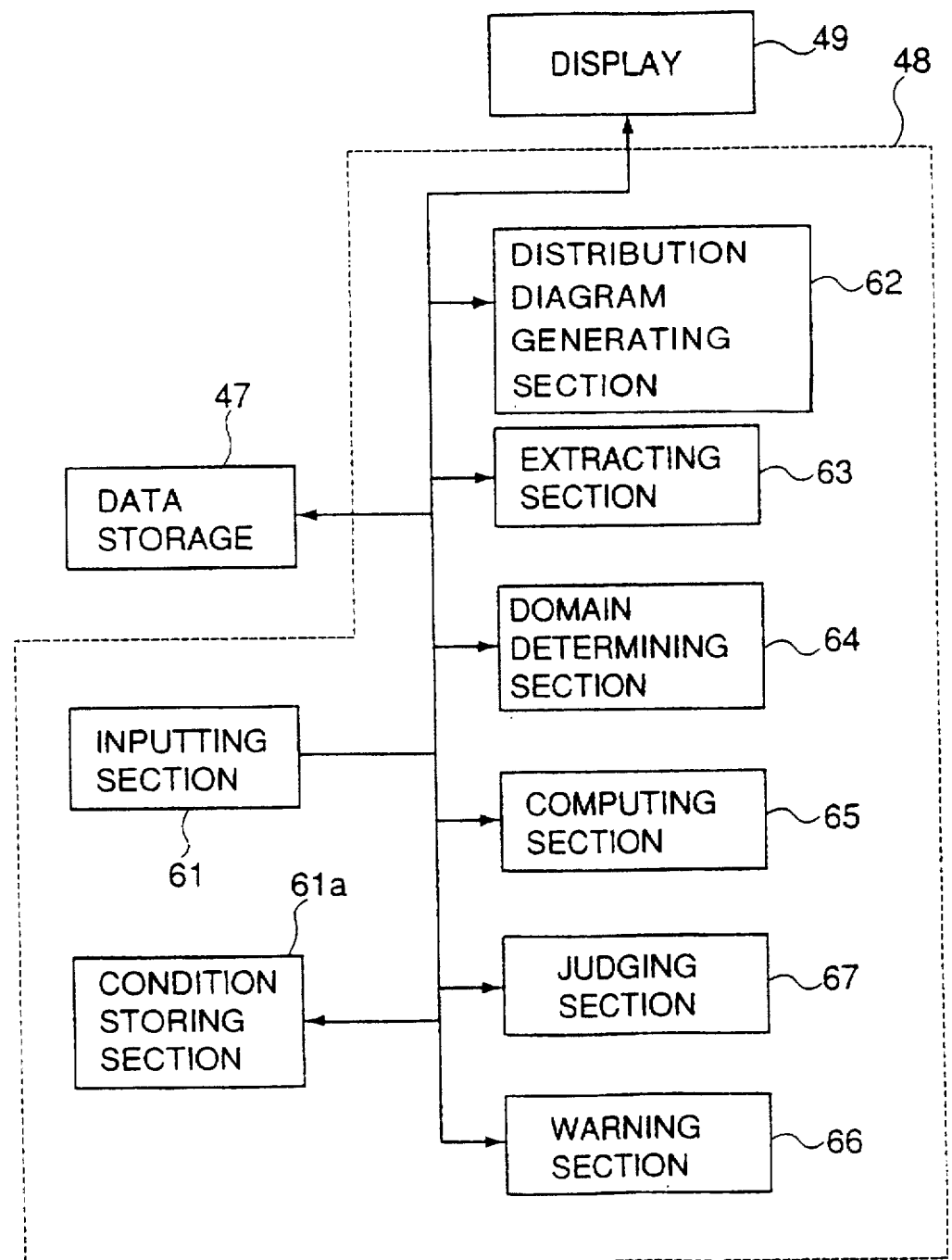
FIG. 4 is a block diagram illustrating the construction of a data processing section shown in FIG. 3.

FIG. 4 is a block diagram illustrating the construction of the data processing section 48. An inputting section 61 is adapted to preliminarily input various conditional data such as conditional values and expectative domains, and comprised of a keyboard and a mouse, for example.

A condition storing section 61a stores the inputted conditional data. A distribution diagram generating section 62 generates distribution diagrams, i.e., Fl-Fsc, Fscw-Fl and Fscw-Flw scattergrams and Fl, Fsc, Flw and Fscw histograms, on the basis of the parameter information stored in the data storage 47. An extracting section 63 extracts coordinate data and domains from the distribution diagrams generated by the distribution diagram generating section 62.

A domain determining section 64 determines domains of the respective material components in the distribution diagrams generated by the distribution diagram generating section 62. A computing section 65 performs various arithmetic operations, and counts data points of a material component in each domain. A warning section 66 gives a warning when an erroneous result on the data clustering or the counting is detected. A judging section 67 determines the kind of the material component particles in the domain. The computation results from the computing section 65 and the warning from the warning section 66 are displayed in the display 49 like the distribution diagrams generated by the distribution diagram generating section 62.

There will next be described principal operations to be performed by the data processing section 48.

(1) Determination of domains in scattergram

Figure 5:
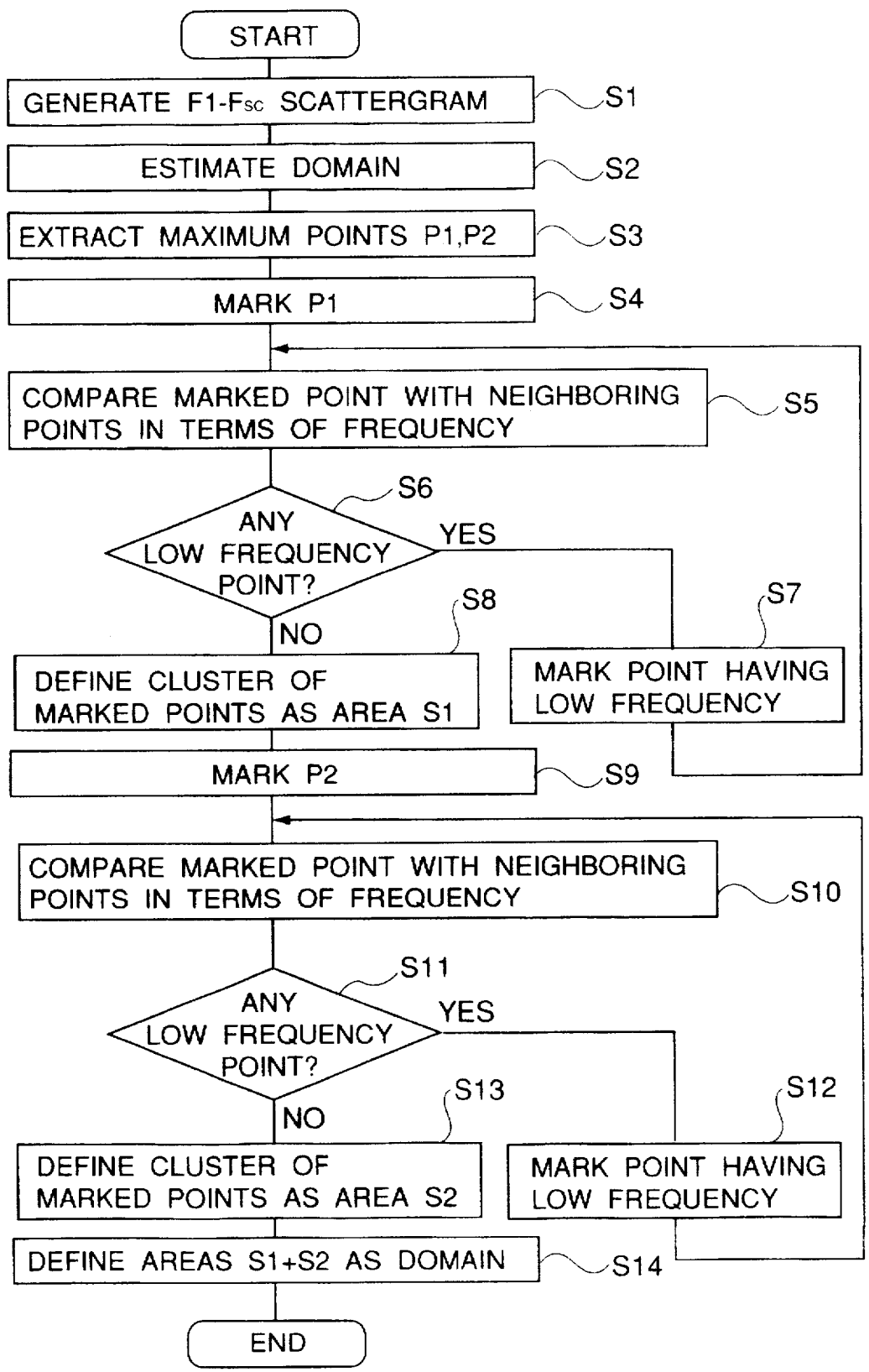
FIG. 5 is a flow chart for explaining an operation to be performed by the data processing section.

In the analyzer, domains of the respective material components are defined in a scattergram for determination of the attribution of the detected material component particles. An exemplary process for the domain determination will be described with reference to the flow chart shown in FIG. 5.

Figure 6:
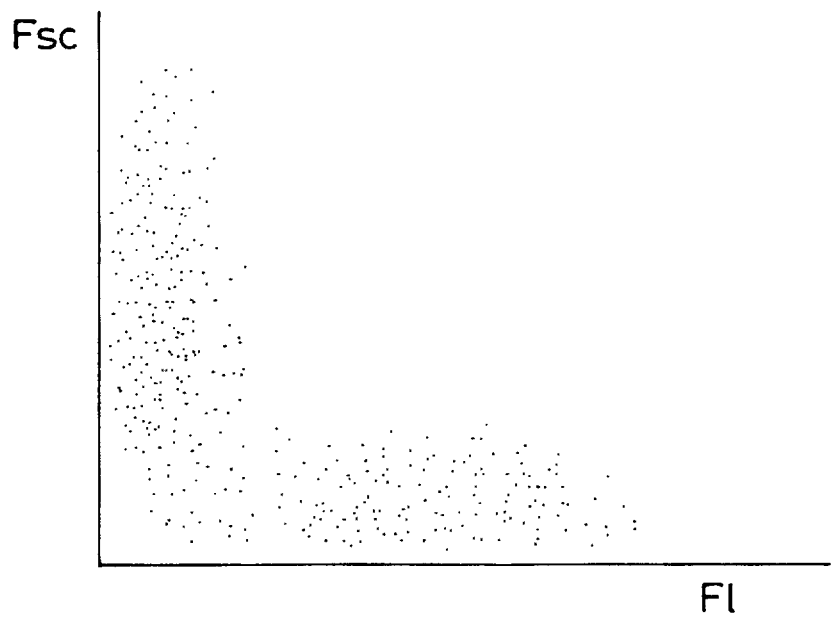
FIGS. 6 to 8 are scattergrams for explaining the operation of the data processing section.
Figure 7:
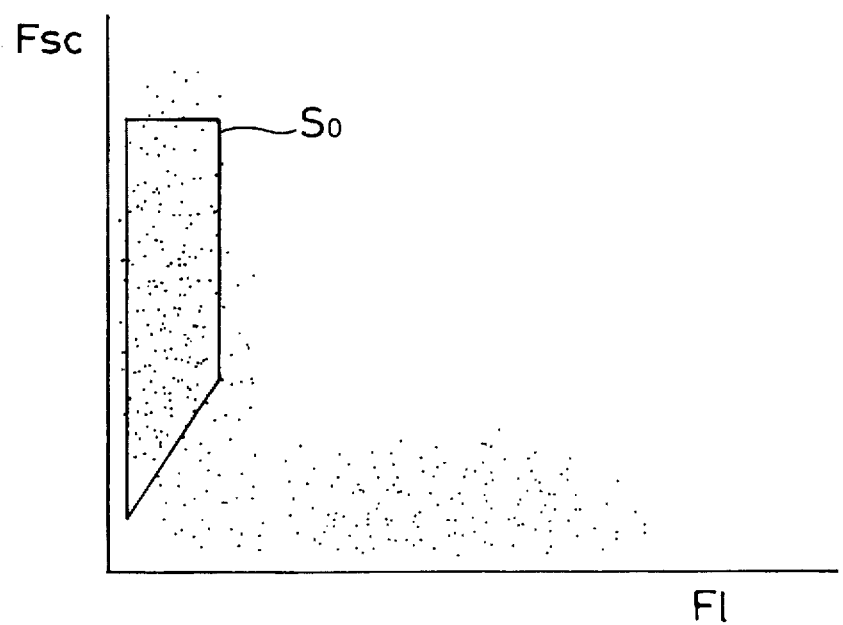

When an Fl-Fsc scattergram is generated by the distribution diagram generating section 62 and displayed as shown in FIG. 6 (Step S1), an expectative domain S0 where the maximum frequency point in erythrocyte distribution is possibly present is read out of the condition storing section 61a, and located in the Fl-Fsc scattergram as shown in FIG. 7 (Step S2). It is noted that an operator can change the location of the expectative domain S0 by operating the inputting section 61.

Figure 8:
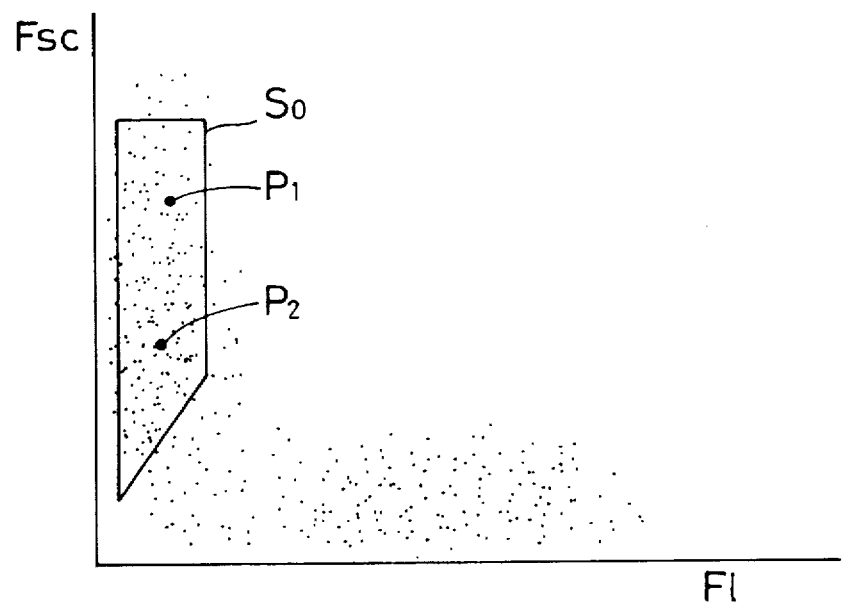

In turn, the extracting section 63 sets a threshold for distribution frequency in the expectative domain S0, and extracts local maximum points P1, P2, . . . each having a higher frequency than the threshold and neighboring points, as shown in FIG. 8 (Step S3).

Figure 9:
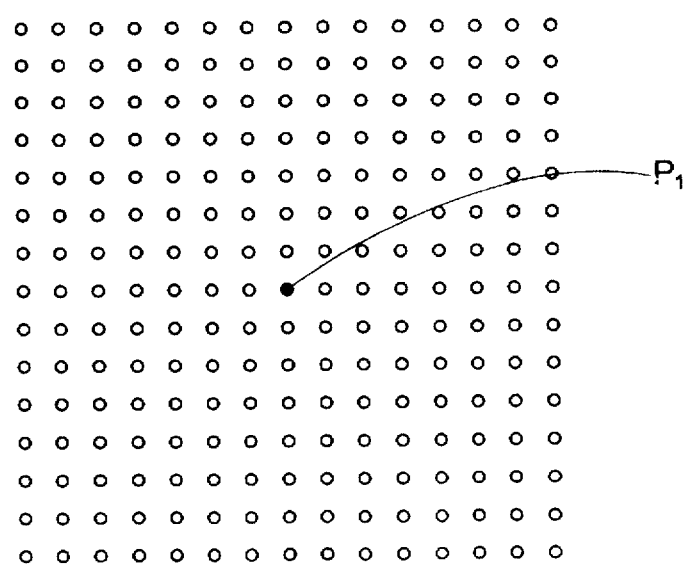
FIGS. 9 to 11 are diagrams for explaining the operation of the data processing section.

As indicated by a solid dot in FIG. 9, the local maximum point P1 is marked as a constituent point of a domain to be determined (Step S4).

Figure 10:
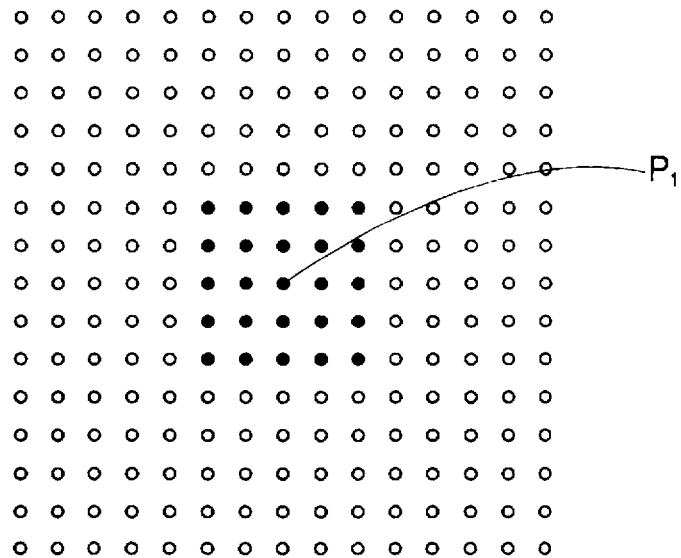
Figure 11:
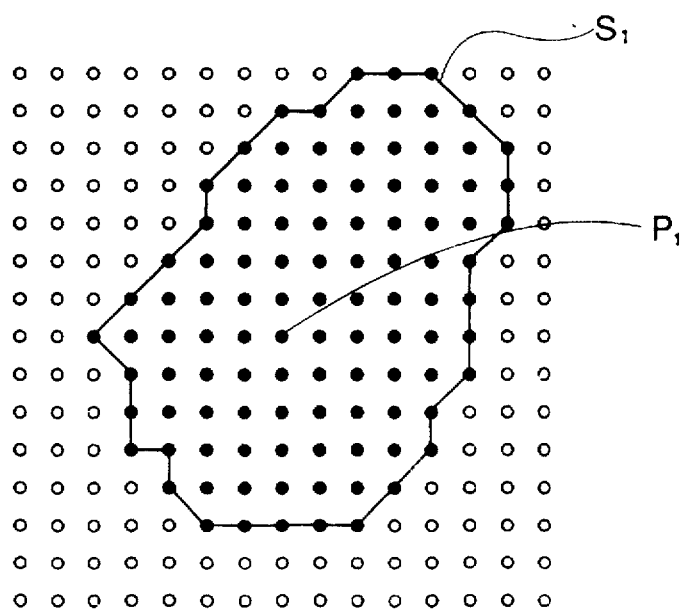
Figure 12:
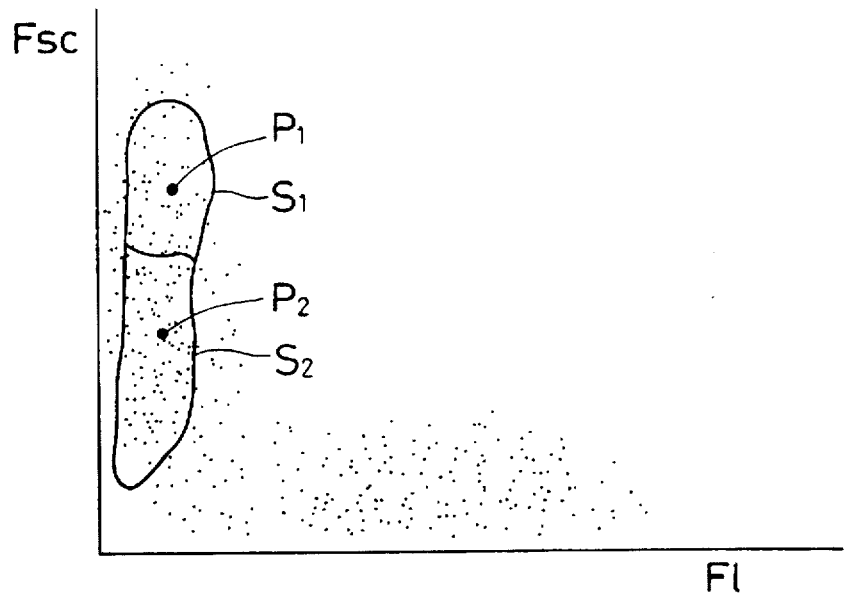
FIGS. 12 to 15 are scattergrams for explaining the operation of the data processing section.

The marked point (solid point) is compared with its neighboring points in terms of the frequency, and then points having a lower frequency are marked as shown in FIG. 10 (Steps S5 to S7). This process sequence is repeated until no neighboring point has a lower frequency than the marked points (Step S6). Then, the cluster of the marked points is defined as an area S1, as shown in FIG. 11.

Where there are a plurality of local maximum points, the process sequence described above is repeated. More specifically, an area S2 for the local maximum point P2 is defined (Steps S9 to S13). Then, combined areas S1 and S2 are finally defined as the erythrocyte domain (Step S14).

Domains of the other material components are defined in the same manner, and the number of material component particles falling within each of the domains is determined by the computing section 65 and displayed in the display 49.

As described above, the domain determining method according to this embodiment is such that one or more local maximum points are first determined and then the domain is gradually expanded by comparing the local maximum points with their neighboring points in terms of the frequency. Therefore, the determination of the domain is not influenced by a complicated configuration of the domain, a large number of local maximum frequency points in the domain, and a small population in the domain.

Even if the distribution of the material component particles is slightly shifted due to a change in the sensitivity of the analyzer, the determination of the domain is not influenced by the shift of the distribution.

Further, coordinate data to be processed can be reduced by consolidating the coordinates of distribution diagrams, whereby the process is simplified for higher speed operation. Where 4×4 coordinates are consolidated, for example, the numbers of distribution diagrams and coordinate data can be reduced to 1/16.

(2) Analysis of erythrocytes in hemolytic state

In accordance with the present invention, erythrocytes in a hemolytic state can be analyzed (the analysis of the hemolytic-state erythrocytes is not performed in the prior-art analyzer). The analyzing process will hereinafter be described.

Figure 13:
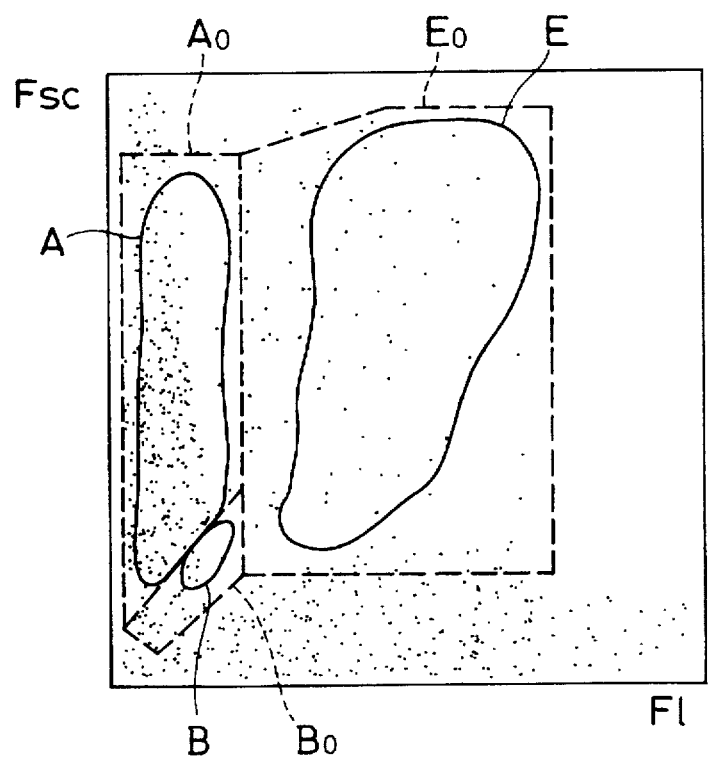

An operator operates the inputting section 61 to input expectative domains Ao, Bo and Eo where maximum frequency points for nonhemolytic-state erythrocytes, hemolytic-state erythrocytes and cryptococcoma-like eumycetes are possibly located, respectively, in an Fl-Fsc scattergram as shown in FIG. 13 in the aforesaid manner. The domain determining section 64 defines an area A where data points of the nonhemolytic-state erythrocytes are mainly located, an area B where the scatter light intensity Fsc is lower than the data points of the erythrocytes in the area A and data points of the hemolytic-state erythrocytes and the cryptococcoma-like eumycetes are located, and an area E where data points of the cryptococcoma-like eumycetes alone are located, as shown in FIG. 13.

Figure 15:
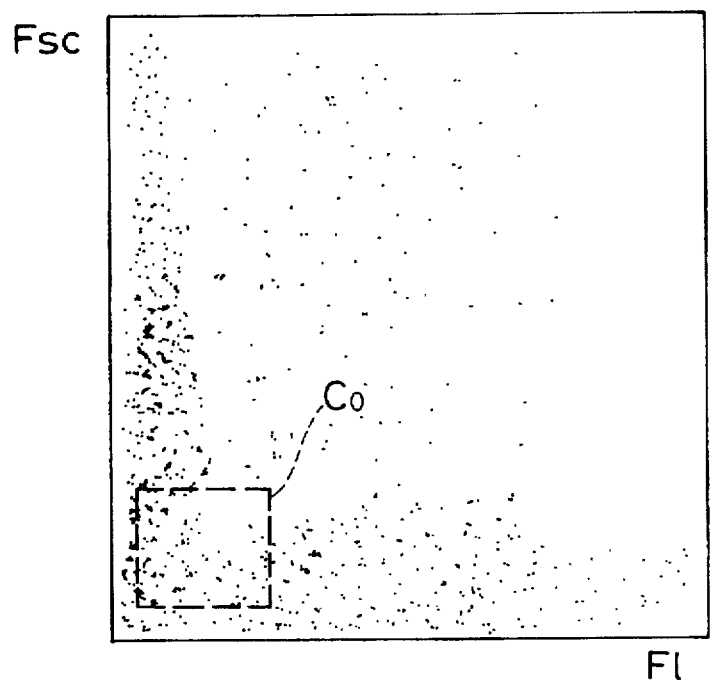

An expectative domain Co where the scatter light intensity Fsc is lower than the data points of the erythrocytes in the area A and data points of the hemolytic-state erythrocytes are possibly located but no data point of streptococcus is present is inputted from the inputting section 61, as shown in FIG. 15.

Figure 14:
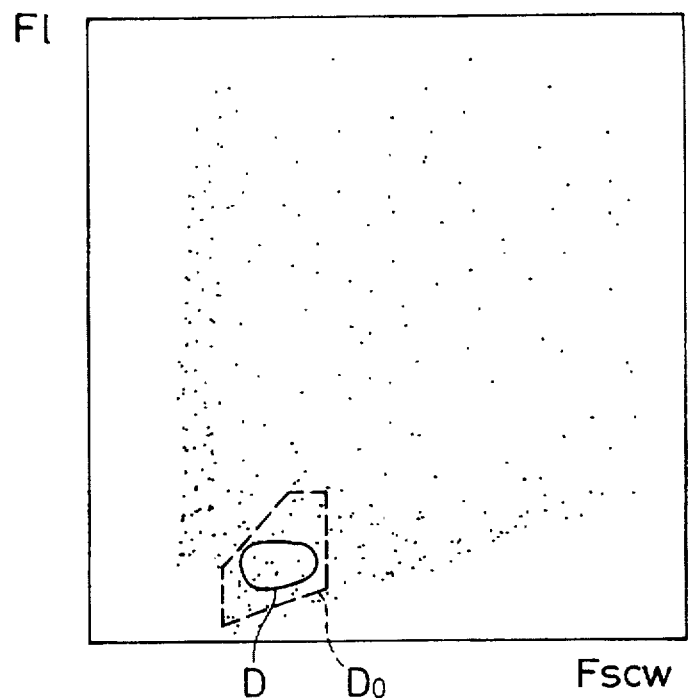

In turn, an expectative domain Do where data points of the hemolytic erythrocytes and streptobacillus are possibly located is inputted in an Fscw-Fl scattergram generated by the distribution diagram generating section 62 as shown in FIG. 14. The domain determining section 64 defines an area D where data points of the hemolytic-state erythrocytes and the streptobacillus are located in the Fscw-Fl scattergram.

The computing section 65 computes the number R of the data points of the nonhemolytic-state erythrocytes in the area A, the number r1 of the data points of the hemolytic-state erythrocytes simultaneously belonging to the areas C and D, the number r2 of the data points of the hemolytic-state erythrocytes in the area B, and the number Y of the data points of the cryptococcoma-like eumycetes in the area E.

The number r of the hemolytic-state erythrocytes and the total number RBC of the erythrocytes are calculated from the following equations:

$$r = r1 + r2 \quad (1)$$

$$RBC = R + r \quad (2)$$

Where the number Y of the cryptococcoma-like eumycetes exceeds a predetermined value e (Y>e), however, there is a possibility that the data points of the cryptococcoma-like eumycetes as well as the data points of the hemolytic-state erythrocytes are present in the area B. Therefore, the data points of the hemolytic-state erythrocytes in the area B is not taken into account, and it is considered that r2=0. On the other hand, if Y≦e, it is considered that the data points in the area B are attributable to the hemolytic-state erythrocytes.

Figure 24:
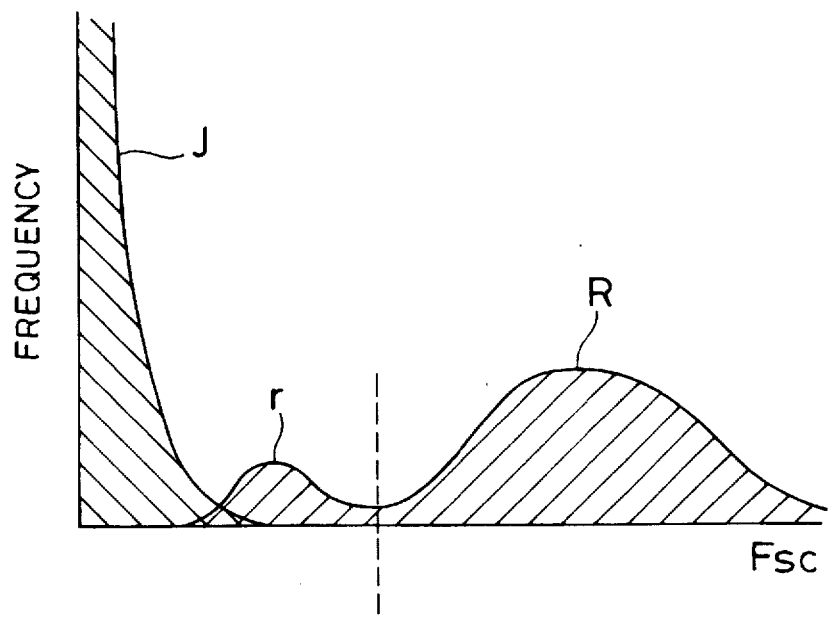
FIGS. 24 and 25 are histograms of erythrocytes in a nonhemolytic state, erythrocytes in a hemolytic state and bacteria.

The number r of the hemolytic-state erythrocytes changes with the lapse of time. For example, the ratio of the nonhemolytic-state erythrocyte number R to the hemolytic-state erythrocyte number r is 80:20 in an Fsc histogram (FIG. 24), but the ratio changes into 20:80 with the lapse of time as shown in FIG. 25.

Figure 25:
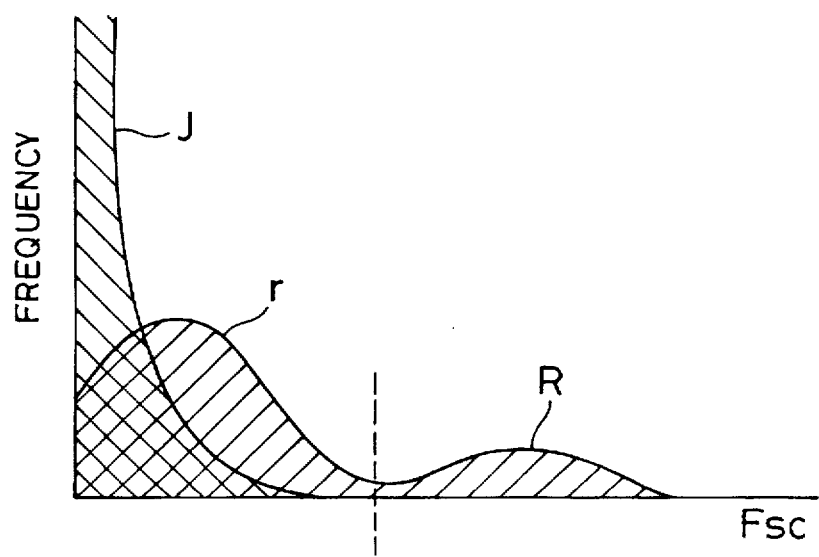

Referring to FIG. 25, a bacteria frequency distribution J significantly overlaps a hemolytic-state erythrocyte frequency distribution r and, hence, the number r of the hemolytic-state erythrocytes cannot accurately be determined. More specifically, if the hemolytic-state erythrocyte number r exceeds a predetermined level, the calculated number r may be erroneous.

Therefore, the area C is an area variably set from the inputting section 61 in consideration of the time-related change in the number of the hemolytic-state erythrocytes.

The computing section 65 computes the ratio h of the hemolytic-state erythrocytes from $h = r/(R+r)$. If the ratio h is greater than a predetermined level, the hemolytic-state erythrocyte frequency distribution overlaps the bacteria frequency distribution. Therefore, the warning section 66 judges that the data clustering is erroneous, and displays a warning in the display 49.

As describe above, the analyzer of the present invention is capable of determining the number of the hemolytic-state erythrocytes (which is not determined in the prior art), allowing for the determination of the total number of the urine erythrocytes. Further, the number of the hemolytic-state erythrocytes can accurately be determined in consideration of the time-related change thereof.

(3) Warning against erroneous analysis (erroneous data clustering)

The analyzer has a function for warning against an erroneous analysis (erroneous data clustering) as described above. In addition, when it is determined that data points of different material components are present in the same domain, the analyzer gives a warning indicative of impossibility of data clustering. An explanation will be given to the warning process, taking as an example the data clustering for the calcium oxalate crystal and the erythrocyte.

Figure 16:
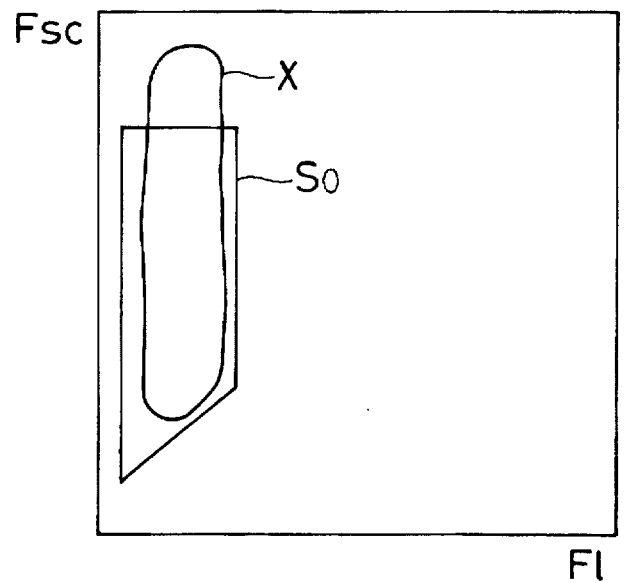
FIGS. 16 and 17 are scattergrams for explaining an operation to be performed by a warning section of the analyzer.
Figure 17:
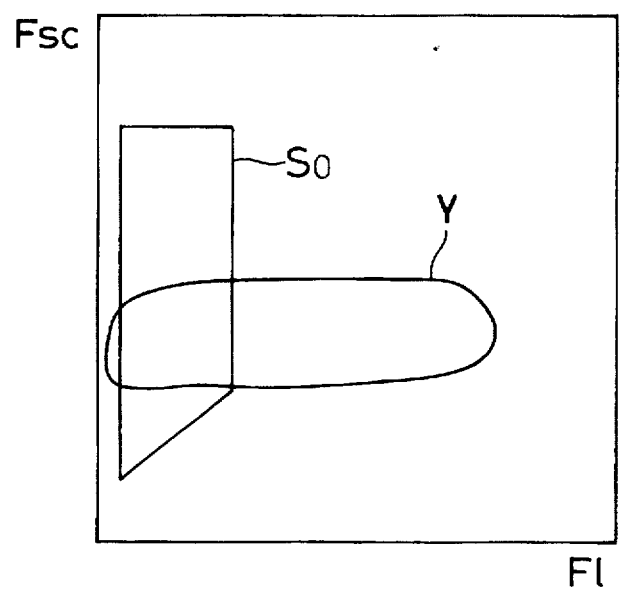

The distribution diagram generating section 62 generates an Fl-Fsc distribution diagram (two-dimensional scattergram) and the domain determining section 64 determines a domain X of the calcium oxalate crystal as shown in FIG. 16. Then, the domain determining section 64 compares the domain X with the preliminarily inputted expectative domain S0 where data points of erythrocytes are possibly located. The domain X of the calcium oxalate crystal mostly overlaps the expectative erythrocyte domain S0, and extends to a higher Fsc level than the domain S0. If it is determined that a difference in the highest Fsc level between the domains X and S0 exceeds a predetermined level, the warning section 66 warns that the data clustering for the erythrocyte is impossible due to the presence of the calcium oxalate crystal.

Where DHA crystal particles are present in a urine sample, a domain Y of the DHA crystal extends across the expectative erythrocyte domain S0 as shown in an Fl-Fsc scattergram of FIG. 17. Therefore, it is impossible to accurately cluster the data points of the erythrocytes.

Figure 18:
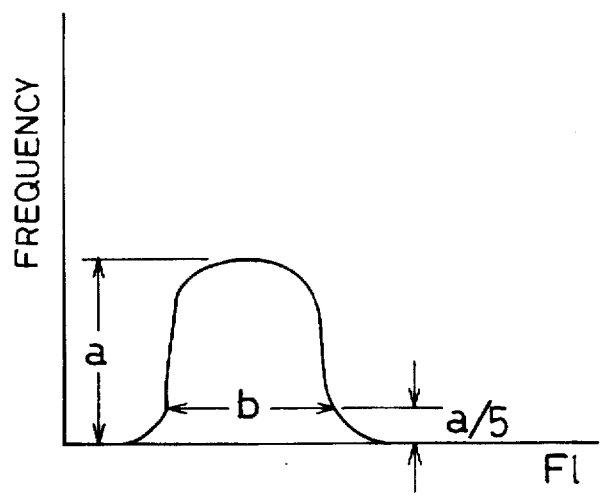
FIG. 18 is a histogram for explaining the operation of the warning section.
Figure 19:
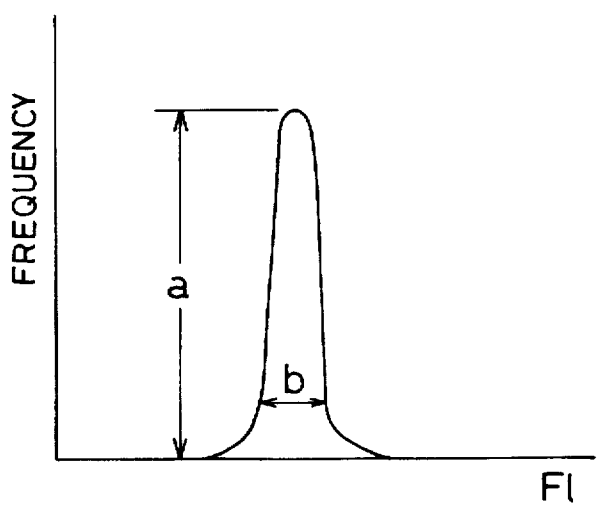
FIG. 19 is a histogram of erythrocytes.

In such a case, the warning section 66 determines the ratio b/a of a peak frequency value a to a distribution range b at a frequency level of a/5 in an Fl histogram (FIG. 18) generated by the distribution diagram generating section 62, and compares the ratio b/a with a predetermined value. The predetermined value is set on the basis of a histogram for typical erythrocyte distribution (FIG. 19). If the ratio b/a exceeds the predetermined value, the warning section 66 warns that the data clustering for the erythrocyte is impossible due to the presence of the DHA crystal.

(4) Detection and subdivision of casts

Where the urine material components (particles) are pretreated by a staining method for staining cell membranes and nuclei, the scatter light emission duration Fscw and the fluorescent light emission duration Flw are roughly equal to each other (Fscw≈Flw) in the case of blood cells, epitheliocytes, bacteria and crystals. In the case of casts containing protein bodies, however, the scatter light emission duration Fscw and the fluorescent light emission duration Flw are different in the level (Fscw>Flw) because the protein bodies are less stainable.

Where casts contain inclusion bodies, only the inclusion bodies are stained and, hence, the ratio of the scatter light emission duration to the fluorescent light emission duration varies depending on the density of the inclusion bodies.

By utilizing such characteristics, the analyzer subdivides the casts into two types, i.e., an inclusion cast and a glass cast (containing no inclusion).

Figure 21:
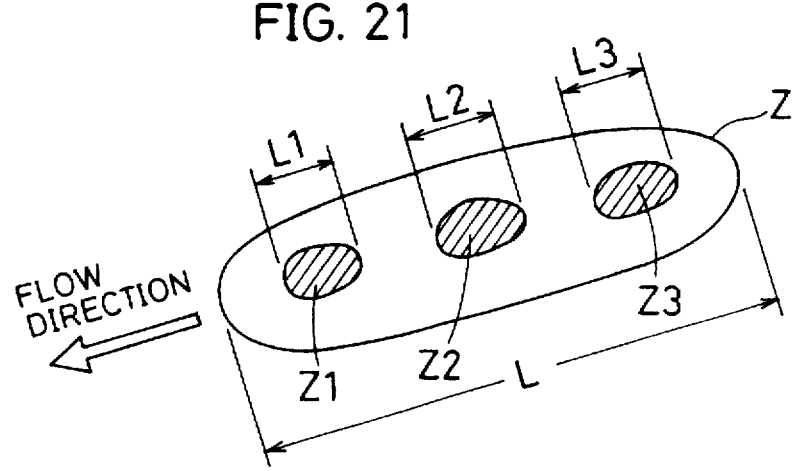
FIG. 21 is a diagram illustrating a cast.
Figure 22:
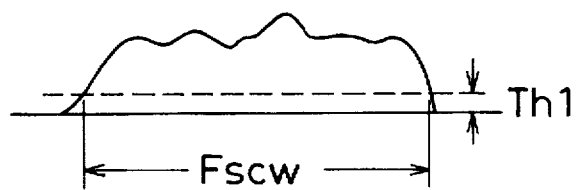
FIG. 22 is a diagram illustrating the waveform of scatter light pulses.
Figure 23:
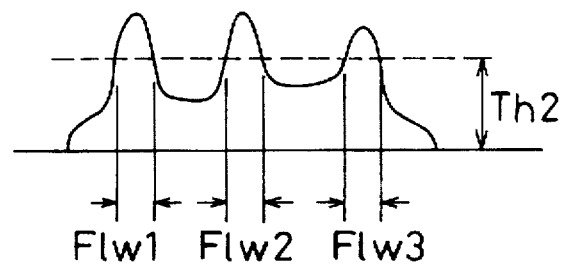
FIG. 23 is a diagram illustrating the waveform of fluorescent light pulses.

More specifically, the length L of a cast Z as shown in FIG. 21 is directly proportional to the scatter light pulse width Fscw shown in FIG. 22. Where the cast Z is preliminarily stained, the lengths L1, L2 and L3 of inclusion bodies Z1, Z2 and Z3 in the cast Z are directly proportional to pulse widths Flw1, Flw2 and Flw3 of fluorescent light signals, respectively, as shown in FIG. 23. It is noted that "Th1" in FIG. 22 and "Th2" in FIG. 23 are predetermined thresholds of the comparators 39 and 37, respectively, shown in FIG. 3.

In the analyzer, the relationship among Fl, Flw1, Flw2 and Flw3 is represented as follows:

$$Fl=Flw1+Flw2+Flw3 \quad (3)$$

Where fluorescent light pulse widths Flw1, Flw2, . . . Flwn are obtained for a single cast, the pulse width Flw for the cast is calculated as follows:

$$Flw = \sum_{i=1}^{n} Flwi \quad (4)$$

In an Fscw-Flw scattergram generated by the distribution diagram generating section 62 on the basis of the pulse width Flw thus obtained, an erythrocyte domain T1, a leukocyte domain T2 and an epitheliocyte domain T3 are located generally along a line L1, while a cast domain T4 is separated from the domains T1 to T3 by a boundary line L2.

Therefore, the judging section 67 defines the domain T4 located below the line L2 as the cast domain.

Alternatively, the determination of the cast domain may be based on the coordinate data in the scattergram. That is, a cluster of coordinate data having Flw/Fscw values smaller than the inclination of the line L2 may be defined as the cast domain.

In general, the amount of inclusion in a cast determines the type of the cast, i.e., the inclusion cast or the glass cast (containing no inclusion).

Figure 20:
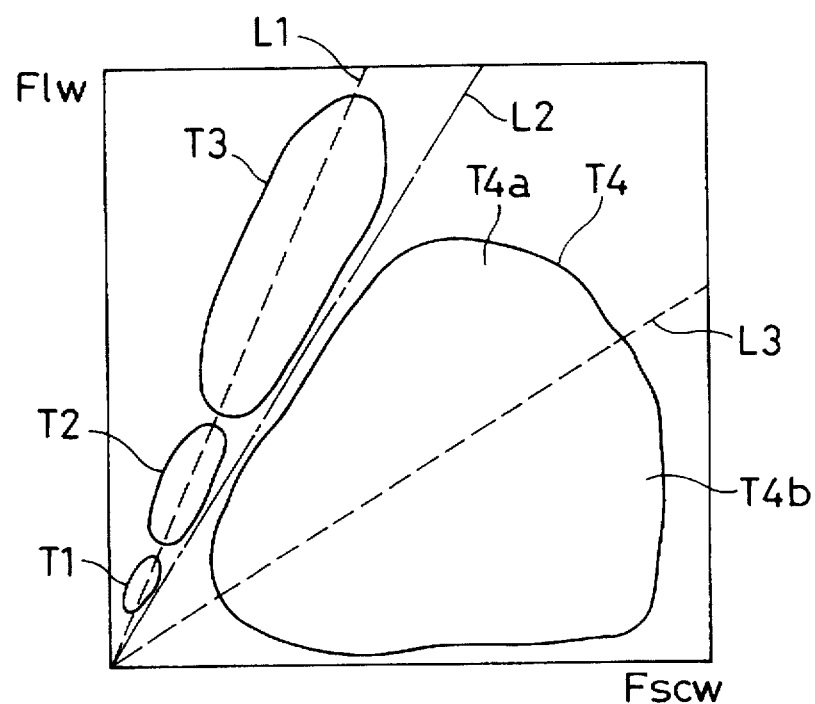
FIG. 20 is a scattergram for explaining domains of respective material components.

Therefore, the line L3 is inputted as a reference for the cast domain determination from the inputting section 61 as shown in FIG. 20. This allows the judging section 67 to define an area T4a above the line L3 as the inclusion cast domain and an area T4b below the line L3 as the glass cast domain.

The analyzer of the present invention allows for easy discrimination of casts from other urine material component particles for determination of the number of the casts. In addition, the analyzer can discriminate between inclusion casts and glass casts containing no inclusion for determination of the numbers of the inclusion casts and the glass casts.

What is claimed is:

1. An analyzer for analyzing particle components in urine, comprising:

a sheath flow cell for forming a sample stream by surrounding a sample liquid containing the particle components with a sheath fluid, the particle components being treated with a fluorescent dye in advance;

a light source for illuminating the sample stream;

a photodetecter section for detecting optical information from the illuminated particle components; and an analyzing section for analyzing the particle components on the basis of the detected optical information;

wherein the analyzing section includes:

a parameter extracting section for extracting a fluorescent light emission duration Flw and a scatter light emission duration Fscw for each of the particle components from the detected optical information;

a distribution program generating section for generating an Fscw-Flw scattergram;

a judging section for judging whether or not the particle components in the scattergram are casts, on the basis of a location of the particle components in the generated scattergram; and said parameter extracting section if fluorescent light emission from a material component particle being analyzed is intermittent, sums up intermittent fluorescent light emission periods for determination of the fluorescent light emission duration Flw.

2. An analyzer as set forth in claim 1, wherein the judging section further includes a function for judging whether or not each particle component contains an inclusion body, on the basis of a location of the particle components in the scattergram.

3. An analyzer as set forth in claim 1, wherein the judging section determines the location of the particle components in the scattergram corresponding to a ratio of the fluorescent light emission duration Flw to the scatter light emission duration Fscw.

4. An analyzer as set forth in claim 3, wherein the judging section determines that the particle components are casts when the particle components are located in an area of the scattergram where the ratio Flw/Fscw is lower than a first predetermined value.

5. An analyzer as set forth in claim 3, wherein the judging section determines that the particle components are casts, when the particle components are located in an area of the scattergram where the ratio Flw/Fscw is lower than 1.

6. An analyzer as set forth in claim 4, wherein the judging section determines that the particle components are casts containing an inclusion body, when the particle components are located in an area of the scattergram where the ratio Flw/Fscw is lower than the first predetermined value and higher than a second predetermined value.

* * * * *

UNITED STATES PATENT AND TRADEMARK OFFICE
CERTIFICATE OF CORRECTION

PATENT NO. : 5,757,475
DATED : May 26, 1998
INVENTOR(S) : Masayuki KATAYAMA et al.

It is certified that error appears in the above-indentified patent and that said Letters Patent is hereby corrected as shown below:

At column 12, line 27 (claim 1, line 23) of the printed patent, change "section" to --- section,---.

Signed and Sealed this

Twenty-fifth Day of May, 1999

Attest:

Q. TODD DICKINSON

*Attesting Officer*  *Acting Commissioner of Patents and Trademarks*